United States Patent
Stolpe et al.

(10) Patent No.: US 9,517,650 B1
(45) Date of Patent: Dec. 13, 2016

(54) PROSTHETIC IRIS PREPARATION METHOD

(71) Applicants: John M. Stolpe, Los Angeles, CA (US); John C. Stolpe, Burbank, CA (US)

(72) Inventors: John M. Stolpe, Los Angeles, CA (US); John C. Stolpe, Burbank, CA (US)

(73) Assignee: John M. Stolpe, Tarzana, CA (US)

( * ) Notice: Subject to any disclaimer, the term of this patent is extended or adjusted under 35 U.S.C. 154(b) by 389 days.

(21) Appl. No.: 13/944,858

(22) Filed: Jul. 17, 2013

(51) Int. Cl.
*A61F 2/14* (2006.01)
*A61F 2/02* (2006.01)
*B41M 5/00* (2006.01)
*A61F 9/008* (2006.01)

(52) U.S. Cl.
CPC .............. *B41M 5/0082* (2013.01); *A61F 2/14* (2013.01); *B41M 5/0041* (2013.01); *A61F 2/02* (2013.01); *A61F 2009/00876* (2013.01); *Y10S 623/905* (2013.01)

(58) Field of Classification Search
CPC ................... B41M 5/0082; A61F 2009/00876; A61F 2009/00872; A61F 2/1605; A61F 2/14; A61F 2/02; Y10S 623/905
See application file for complete search history.

(56) References Cited

U.S. PATENT DOCUMENTS

| | | | | |
|---|---|---|---|---|
| 1,993,121 A * | 3/1935 | Travers | .................... | A61F 2/141 351/159.02 |
| 2,653,328 A * | 9/1953 | Anderson | .............. | B29D 11/02 623/6.64 |
| 2,673,984 A * | 4/1954 | Clarke | .................... | A61F 2/141 623/6.64 |
| 6,143,026 A * | 11/2000 | Meakem | ................ | A61F 2/141 128/898 |
| 6,746,120 B2 * | 6/2004 | Broderick | .............. | G02C 7/046 351/159.69 |
| 7,029,608 B1 * | 4/2006 | Lewis | ....................... | A61F 2/14 156/61 |

(Continued)

*Primary Examiner* — Alison L Hindenlang
*Assistant Examiner* — Jerzi H Moreno Hernandez
(74) *Attorney, Agent, or Firm* — Cislo & Thomas, LLP; Kelly W. Cunningham, Esq.

(57) ABSTRACT

A method and system for making digitized iris prints for prosthetic eyes in a consistent, efficient, and cost-effective manner using digitally created and stored irises. A database of known iris colors and characteristics can be stored and associated with unique quantitative identifiers. An ocularist is provided with an array of sample irises containing known iris colors and characteristics matching the iris colors in the database. Each sample iris has unique, scientific, reproducible quantitative markers or indicia. The ocularist can select one sample iris from the array where the iris color and characteristic most closely matches the natural eye. The selected sample iris can be identified by its unique quantitative markers, and vice versa. The identifier can be looked up in the database of known iris colors. Furthermore, by applying the tools of the digital age to an artistic skill and trade that goes back many decades, a new easy-to-reproduce iris with appropriate modification to selected markers for a digitized iris print can be created and used for the new prosthetic eye. Accordingly, maximum success is achieved by maintaining control of technical variables which include, but are not limited to, hue, saturation, brightness, iris dimensions, and effect of clear PMMA encapsulation.

7 Claims, 4 Drawing Sheets

(56) References Cited

U.S. PATENT DOCUMENTS

2005/0275137 A1* 12/2005 Stolpe ................... A61F 2/14
                                                    264/294
2013/0317609 A1* 11/2013 Green ................... A61F 2/141
                                                    623/6.64
2014/0161325 A1*  6/2014 Bergen ................ G06K 9/0061
                                                    382/117

* cited by examiner

PROSTHETIC IRIS PREPARATION METHOD

TECHNICAL FIELD

This invention relates to the preparation of irises for prosthetic eyes, and more particularly to the preparation of such irises using photographed irises that are digitally processed, in concert with an array of prefabricated sample irises for which unique, scientifically reproducible quantitative markers or indicia are identified.

BACKGROUND

Artificial eyes date back to ancient times, when pharaohs would have their eyes surgically removed and replaced with gold eyes so people would think they were gods. More recently, going back to the 1600's, eye prosthetics were made of glass. With the invention of modern plastics came the new acrylic eye, which has several advantages over traditional methods.

While many people believe that prosthetic eyes are only for individuals missing an eye, in fact this is not the case. Out of the millions of eye injuries that occur every year, many people keep their damaged natural eye intact. Though it may lose vision or appear unsightly, eyes can (and should) remain healthy organs within an individual's anatomy. The reason for this is multifold. Ocular health can be better maintained when an eye remains in its socket. Also, when it comes time to fit a person with a prosthetic eye, much more natural movement and look can be achieved when fitting the piece over an existing, albeit deformed, natural eye. It is very important to understand this, as patients can sometimes be led by ophthalmologists or ocular surgeons to remove an eye that could otherwise be saved. This is because removing an eye is often the cheapest, easiest treatment. It may not, however, be best for the longterm quality of life of the patient.

Occasionally patients are diagnosed as non-visioned, but have some light perception, or patients have avoided being fitted with prosthetic eyes because of the implications of losing their light perception. It may therefore be very important to utilize any available vision when possible, rather than cover the eye with an opaque, artificial iris and pupil that would eliminate any light perception. This is particularly important in children who are still developing their neural pathways, so that they may still receive the light stimuli through the pupil and into the brain so that those neural pathways do not shut down. Additionally, a small or underdeveloped eye in a child may benefit from the stimulation of the prosthesis that keeps the face growing.

Getting the iris color right, as well as its shape and internal structures, is very complex. Most ocularists still have irises and neighboring sclera painted by hand because digital photography in preparing an iris is a complex matter. Mastering digital coloration is said by many to be impossible.

People have been creating eyes by hand going back to ancient Egyptian times—from metals, to glass, and most recently oil paints on acrylic or silicone eyes. The artists have gotten extremely sophisticated with different methods of reproducing a patient's color. Often, the artist paints in front of a patient or a photograph of the patient.

There are instances where someone may be happy with the fit of their prosthetic eye, but they do not love the prosthetic eye colors—perhaps the iris looks grainy, or it is a low resolution where brush strokes are visible. In these cases, the textural difference draws attention to the prosthesis, making it look different from the natural eye. Despite the painstaking work required, the colors will not always match.

A truly detailed, hand-painted artificial eye takes several hours of work. While a skilled artist can match with a high degree of accuracy, if there is ever any problem with the piece or a mere "slip of the wrist," which ruins the color during the multi-step manufacturing process, the ocularist may have to start over, incurring lost time and costs of painting an entirely new iris.

For the foregoing reasons, there is still a need for a system and method that can take the infinite colors of the eye, and turn them into a digitally reproducible system that is safe, consistent, efficient, long lasting, and cost-effective.

SUMMARY

The present invention is directed to a method and system for making prosthetic irises and eyes in a consistent, efficient, long-lasting, and cost-effective manner that is safe for the patient using digital technology.

An object of the present invention is the integration of digital technology into ocular prosthetics. Using the latest digital photography tools, eyes can be observed and recorded like never before. Digital printing can be done at resolutions from 300 to 2400 dpi (dots per inch), and beyond. With the present invention the patient's iris can be more precisely duplicated and refined. Superior replication can be achieved in an efficient manner. An ocularist can numerically record one or more factors with much more ease than an artist who must start hand painting from scratch with materials squeezed from an artist's paint tube. By starting from an array of eye colors which are molded inside cornea material and laid out in organized fashion on a digital starter board or kit described in the application, color can be refined easily by an ocularist, and more energy can be spent on perfecting the shape.

In some embodiments, a starter kit of 84 digitized iris prints may be provided that may cover the largest possible range of the population. A larger kit or library of digital prints will add to the reproducible number of colors and structures that will make the color matching process even more accurate and efficient to reproduce a patient's iris. The method and system offers the ability to order irises remotely over the Internet to create custom composite prosthetic eyes.

In some embodiments, a transparent pupil can be created in the artificial eye so that patients can use what vision they have, or opaque ocular prosthesis may be used to reduce confused light stimulation to the brain.

Artificial eyes are totally customized in every way. The veining patterns are uniquely matched. Even the limbus (the outer ring that blends from the white to the color) is uniquely created. The nuances in the white sclera may also be captured.

The first step in creating a prosthetic eye is an initial consultation. The ocularist will inform the patient of the best options to treat his or her condition. Next is the fitting step. When fitting a patient for prosthetic eyes, the ocularist begins by taking an impression of the ocular socket by taking a mold—much like a dental impression—of the eye and the space around it. Then an extremely accurate iris is created using cutting edge digital technology to replicate the patient's other (natural) eye, by comparing the natural eye with an array of sample irises containing a wide variety of eye colors. Once the "visual art" component of the piece is complete, the ocularist encapsulates the digitized iris print layer in a final iris and proceeds to refine the fit of the patient's eye.

DETAILED DESCRIPTION OF THE INVENTION

Figure 1:
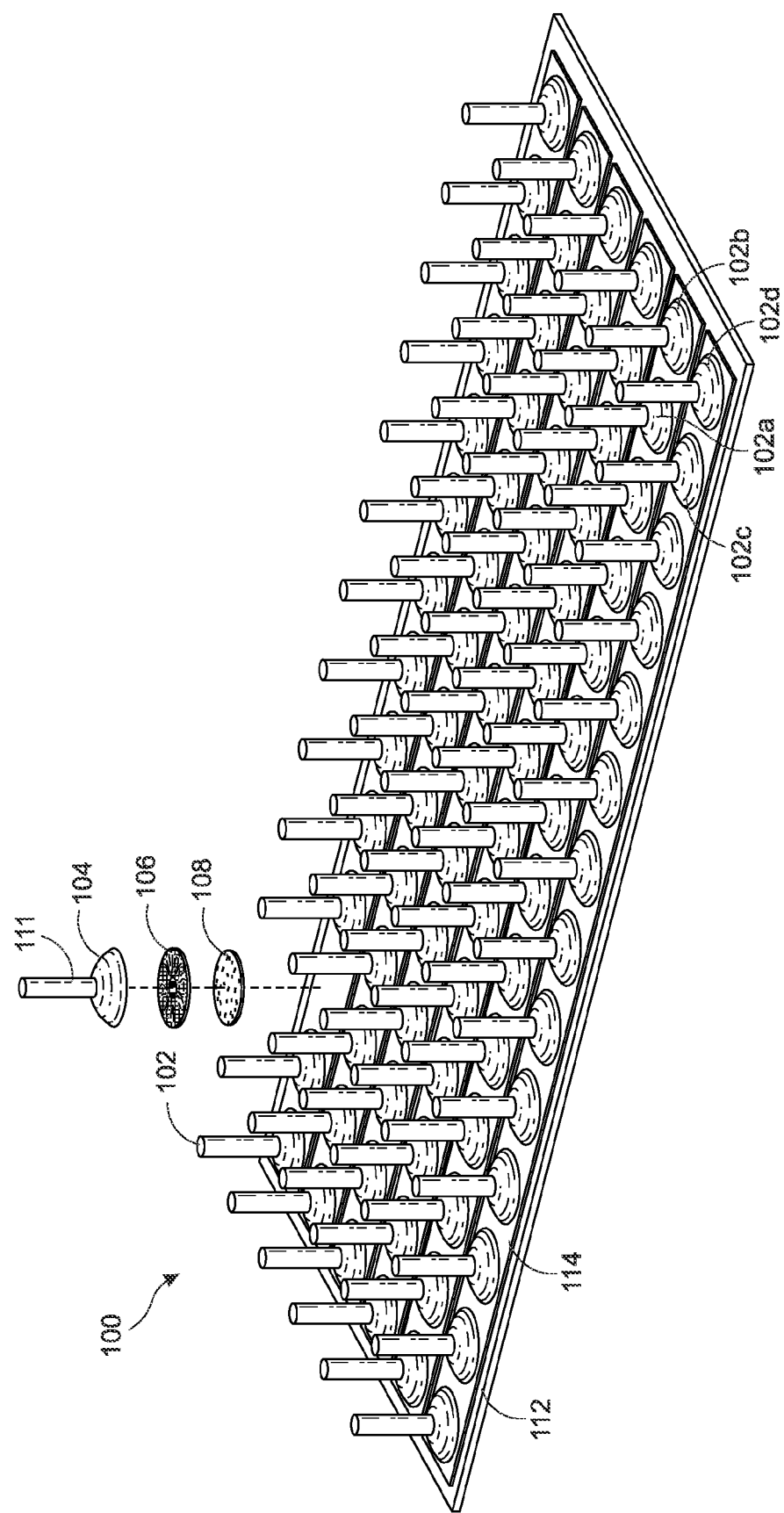
FIG. 1 shows a perspective view of an embodiment of an array of sample irises.

The detailed description set forth below in connection with the appended drawings is intended as a description of presently-preferred embodiments of the invention and is not intended to represent the only forms in which the present invention may be constructed or utilized. The description sets forth the functions and the sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

In general, the prosthetic iris preparation method begins with the initial consultation, to manufacturing of the eye, to follow-up care. The first step is to find out exactly what the patient needs and make a plan on how to achieve the patient's goals. At any time, an extremely high quality photograph of the patient's functioning eye may be taken to use as a template for the manufacture of the prosthetic eye so that all of the visual detail can be incorporated into the prosthetic eye. For example, the photograph of the functioning eye can be taken before the impression is made.

Once the initial consultation is complete and a prosthetic eye is determined to be the best option, an impression of the eye socket is made using known techniques. In general, an impression tray is inserted into the eye socket that will be receiving the prosthetic eye. The impression tray has a hollow stem leading into the eye socket. A dental casting gel, such as alginate or silicone, is forced into the hollow stem with a syringe. The casting gel then fills the entire eye socket, thereby creating the impression. The impression can then be used to create a mold of the eye socket. This mold will serve as the starting point for the overall shape of the final product.

The mold may be used to create a clear acrylic shell or the scleral shell used for the purposes of shaping and fitting in the eye socket. This may take place over the course of two to five appointments, and over a range of one day to six months. While the initial shell can be very close to the patient's needs, a trial period using the initial shell is extremely important. This allows the patient to see how he or she feels wearing this shape of the shell, i.e., whether the shape fits, is comfortable, feels natural like the other eye, etc. Additionally, the curvature of the eye may adjust to the initial shell that goes over it.

In the meantime, the final iris may be created. The final iris can actually be made at any time after the initial consultation. Traditionally, the iris was hand-painted onto a disk to match the functioning eye. The color on the disk is compared to the patient who must, therefore, be present. Once the color was matched to satisfaction, the disk was attached to a cornea. Oftentimes, however, the iris color of the finished prosthetic eye ended up being different compared to the natural eye because the final encapsulated product was not the same as the product that was compared for color matching purposes. In other words, the color matching of the painted iris for the prosthetic was done by comparing the iris color before being print-embedded into the acrylic with the natural eye. In the final product, however, the iris was encapsulated in the cornea; therefore, some changes in the perceptible color scheme occurred due to the processing, and the prosthetic iris color could be evaluated only after the color changes have taken place. Without the ability to evaluate the final color, often in the past, this resulted in the ocularist or artist having to re-paint the iris all over again.

In the present invention, however, the iris is digitally created on a computer, printed on special paper, and encapsulated in a sample cornea 104. Through much experimentation, it has been that, if the color of two digital images match on a computer screen, they will also match when properly printed and molded into a polymethyl methacrylate (PMMA) cornea. Therefore, even though a printed digital image or image on a computer screen may not match an encapsulated iris, if the indicia matches, it will be the correct iris color because the match was based on an encapsulated iris. In order for the printed digital irises to remain color stable and not noticeably fade over the five- to seven- or more year life of a normal plastic prosthetic eye, the inks and media on which they are printed must be completely resistant to the strong chemical effects of PMMA.

Figure 3:
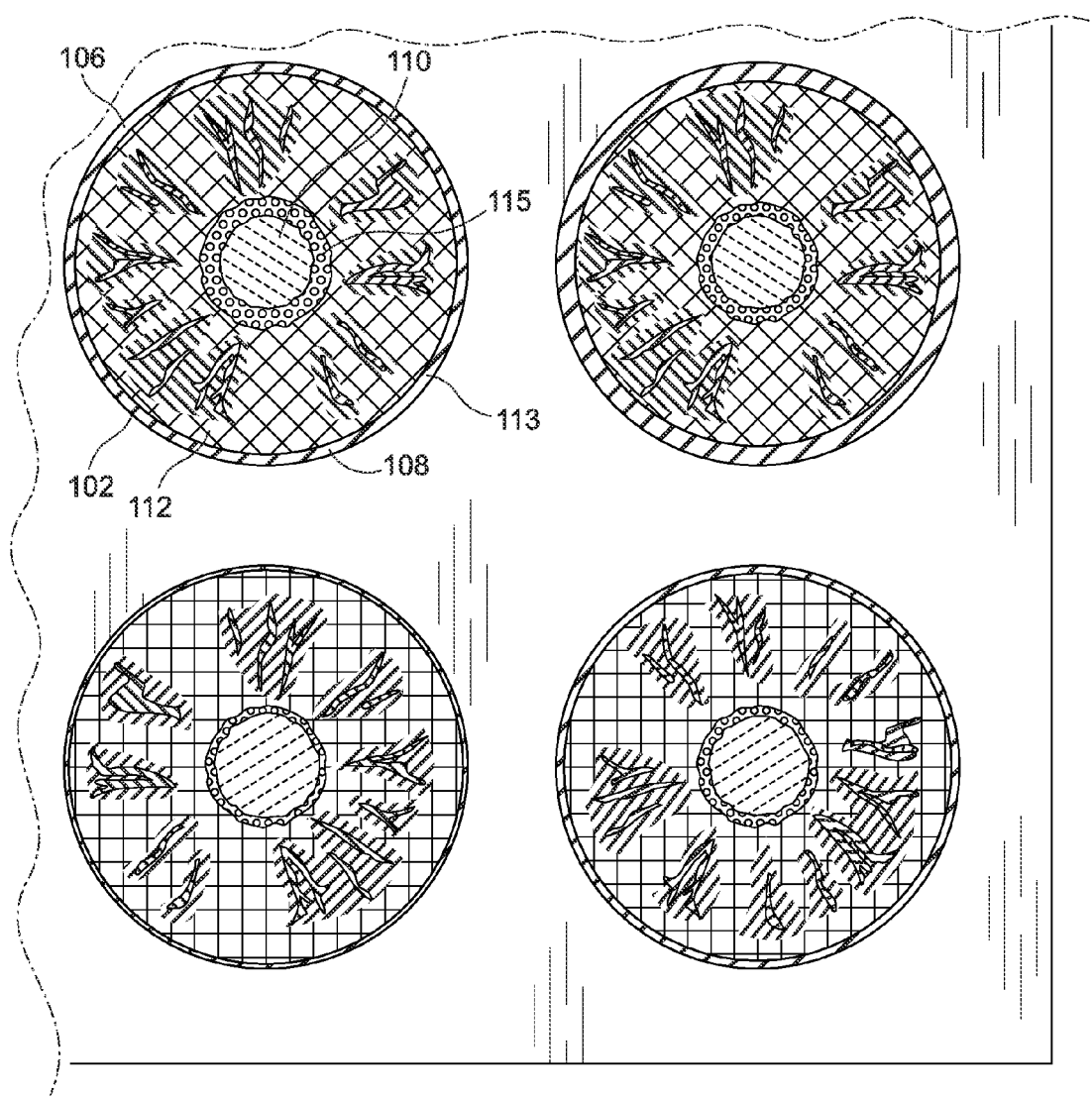
FIG. 3 shows a close-up of the sheet of digitized iris prints shown in FIG. 2.

The comparison for a matching color is done by matching a sample iris 102 containing a sample iris layer 106 encapsulated in a sample cornea 104 to mimic the natural eye so as to avoid changes that might occur during further processing of the prosthetic eye. In order to match the iris color, the ocularist has an array of sample irises 100 containing a set of known iris colors, as shown in FIG. 1. Each sample iris 102 comprises the sample cornea 104, a specific or unique iris layer 106, and a backing 108 containing a unique indicia or identifier (not shown). The backing 108 encapsulates the unique iris layer 106 in the sample cornea 104. As shown in FIG. 3, the unique iris layer 106 may comprise an outer ring or limbus 113, a body or stroma 112, and an inner ring or collarette 115. The limbus 113 defines the periphery of the iris and surrounds and borders the body 112. The inner ring or collarette 115 directly surrounds the pupil 110 and defines the borders of the pupil 110. The body 112 lies in between and is bordered by the limbus 113 and the inner ring 115. The limbus 113, the body 112, and the inner collarette ring 115 may be different colors.

In some embodiments, the array of sample irises 100 may comprise essentially all known iris colors, including the different colors of the limbus 113 and inner ring 115. The ocularist uses the array of sample irises 100 to select the sample iris 102 most closely matching the natural eye. Once selected, the ocularist identifies the selected sample iris by its unique indicia or identifier 110, for example, on the backing 108. The indicia or identifier may be a name, a number, a letter, a series of letters, a series of numbers, and the like, or any combination thereof. Once the unique indicia has been identified, the ocularist need only to search for the indicia in a database and have a computer identify further quantitative data of color and other dimensional indicia with which a final digital iris is produced. Once the final digital iris associated with the unique indicia has been identified and selected, along with appropriately quantifiable intricacies, that final digital iris may be printed as a digitized iris print 402 and incorporated into the final iris 400.

By way of example only, the array of sample irises 100 may contain 84 shades of known iris colors with each sample iris 102 being identifiable by unique indicia. In other embodiments, the number of sample irises in the array may be sufficient to cover every known shade of eye colors. This allows the ocularist to compare the sample irises 102 (having a sample of the final polymer coating and sheen) to the natural eye of the patient to find an exact matching color. Not only does this allow the ocularist to match eye color, but it also allows the ocularist to match other characteristics of the iris. For example, besides the color of the iris, the ocularist may be able to match the color and physical (dimensional) characteristics of the outer ring and inner ring characteristics of the natural eye as well.

In another embodiment, to facilitate such a process, the final, complete digital sample irises 102 may be arranged systematically in groups according to certain characteristics of the eye or iris, such as eye color, inner ring color, inner ring dimension, limbus color, limbus dimensions, and the like. Within each group, the digitized iris print layer 106 may be arranged systematically according to increasing or decreasing shade, hue, dimension, or degree of pronouncement. For example, all the brown colored irises may be grouped and arranged systematically from the lightest shade of brown to the darkest shade of brown, or vice versa. This kind of grouping and arrangement can be done for each eye color and shade known. Similarly or alternatively, the irises may be grouped and arranged systematically from the least pronounced limbus to the darkest limbus, or vice versa, and/or the narrowest potential limbus to the thickest limbus, or vice versa. Such an arrangement also displays lightness/darkness variations so that another ocularist can use the unique indicia to further define an appropriate color for the patient.

In some embodiments, the array of final, complete sample irises 100 may be presented on a tray 112 as shown in FIG. 1. The tray 112 may have a reversible fastening mechanism 114 that allows the sample irises 102 to be removed from the tray 112 and placed securely back on the tray 112. In the preferred embodiment, the tray 112 may have an adhesive so that the sample irises 102 can be repeatedly removed for close inspection or comparison and then stuck back onto the tray 112.

If the patient has brown eyes, the ocularist can go to the section on the array 100 with brown irises, then systematically compare all the sample irises 102 having brown hues and compare each to the natural eye until the correct shade is discovered. The ocularist can pull each candidate sample iris 102 off the tray 212, compare it to the natural eye, and if not a match, place the candidate sample iris 102 back on the tray quickly and easily. This process can be repeated for the other characteristics of the eye, such as the limbus 113 and inner ring 115, as well as any noted radial structures in the patient's natural iris.

In some embodiments, each sample iris 102 may comprise a stem 111 sticking out from or near the apex of the cornea to facilitate holding the sample iris 102. In some embodiments, the stem 111 is not required.

If the final, complete sample iris 102 is a match, then the ocularist can turn the sample iris 102 over and look at the unique indicia on the backing. In some embodiments, the sample irises 102 may have a stem 111 that the ocularist can grab to easily look for the unique indicia. In some embodiments, the tray 112 is transparent so that the ocularist can see the indicia through the tray. In other embodiments, the indicia are repeated on the back of the tray for the location for the given sample iris. The ocularist then goes to the computer and looks up the unique indicia and has the iris printed on special paper to be incorporated into a final iris 400. A code, such as a bar code, QR code, or the like, can also be used as the unique indicia to incorporate more information, such as the date of manufacture, the lot number of inks, or the acrylic batch used.

Figure 2:
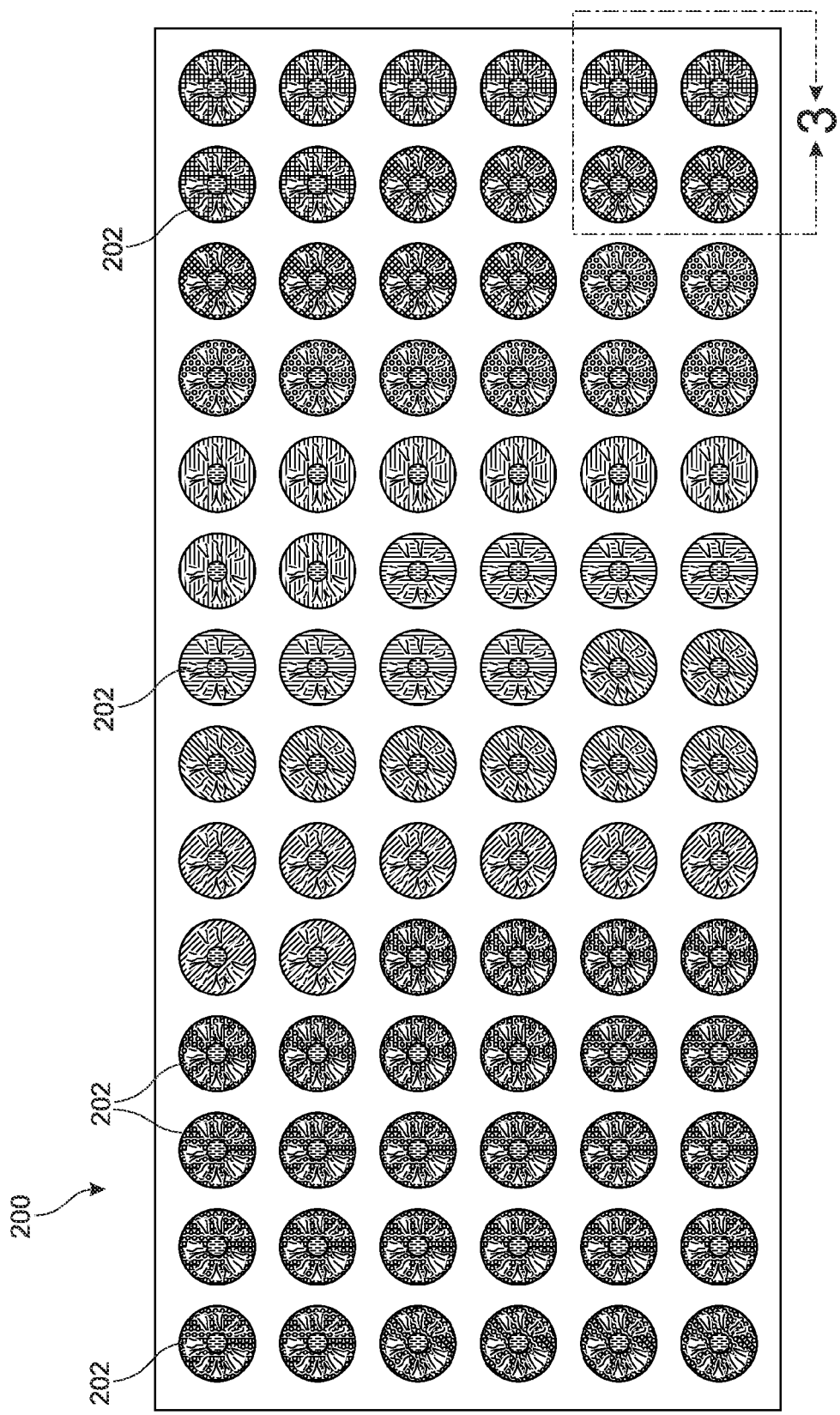
FIG. 2 shows a top view of a sheet of digitized iris prints.

In some embodiments, as shown in FIG. 2, there may already be pre-printed irises 202 in stock 200 that can be incorporated into a final iris 400 or even a pre-formed final iris with a particular shade and color already in stock. In any event, since the color was matched based on the sample iris, which accounts for the shade and color when the cornea is in place, the room for change in color is significantly minimized or practically eliminated.

In some embodiments, the ocularist may mix and match features from two or more sample irises 102 to create a composite iris of multiple intricacies and unique characteristics so as to more closely match to the natural eye. For example, the ocularist may select a first sample iris 102a that most closely matches the body color of the natural iris, a second sample iris 102b that most closely matches the limbus of the natural iris, a third sample iris 102c that most closely matches the inner ring of the natural iris, and a fourth sample iris 102d having other similar radial structures. Each of these sample irises 102a-d has its own unique identifier. Therefore, in this example, the ocularist can select the first sample iris 102a as identified by a first identifier for the body 112, the second sample iris 102b as identified by a second identifier for the limbus 113, the third sample iris 102c as identified by a third identifier for the inner ring 115, and the fourth sample iris 102d as identified by the similarities in radial structure. The identifiers can be inputted into a computer so that the body 112 associated with the first identifier is combined with the limbus 113 associated with the second identifier and the inner ring 115 associated with the third identifier to create a composite that matches the natural eye of the patient.

In some embodiments, the ocularist may select additional sample irises to match other characteristics of the eye or iris, such as the proper shade or hue of the body 112, limbus 113, and/or inner ring 114. In some embodiments, the thickness or the dimensions of the body 112, limbus 113, and/or inner ring 115 may also be determined by comparing the natural eye to the sample irises 102 and selecting sample irises 102 matching the natural eye to create the matching iris. Other miscellaneous structural characteristics of the body 112, limbus 113, and/or inner ring 115 may be used to assure the closest match to the natural eye possible. Therefore, the ocularist can mix and match the color, shape, and dimensions of multiple sample irises 102 and use the indicia of each sample iris 102 to produce a final iris 100 that is a composite of the selected sample irises 102 so as to create an iris that most closely matches the natural eye of the patient.

Figure 4A:
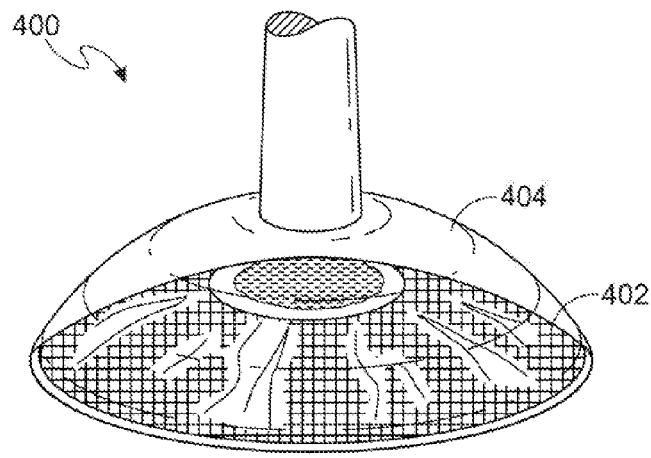
FIG. 4A shows a top perspective view of an embodiment of a sample or final iris.
Figure 4B:
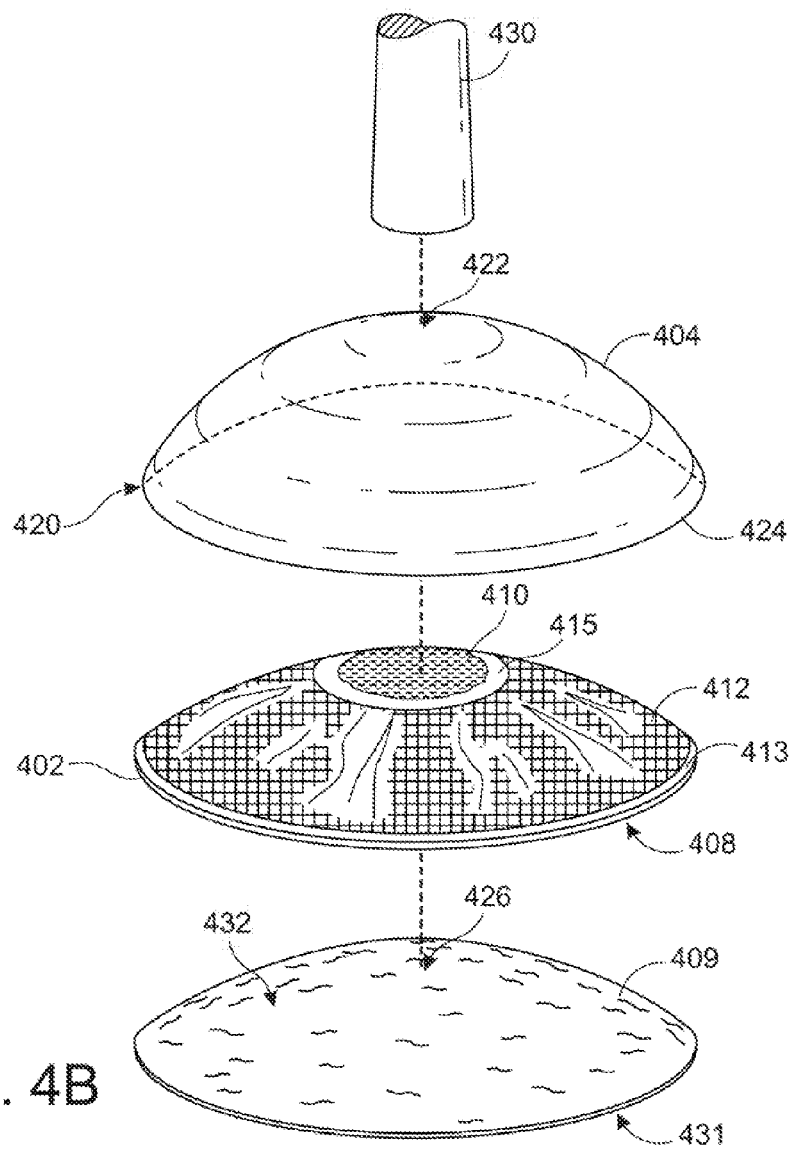
FIG. 4B shows an exploded view of the embodiment shown in FIG. 4A.

With reference to FIGS. 4A and 4B, in the preferred embodiment, the iris color should be printed on special media 408 with companion inks that are completely resistant to the strong chemical effects of PMMA to create a digitized iris print 402 for longevity purposes. The digitized iris print 402 has a center portion or pupil area 410 and body portion 412 surrounding the center portion 410. The main body portion 412 comprises one of the known eye colors. The main body portion 412 may be surrounded by the limbus 413 that borders the main body portion 412. An inner ring 415 may surround the center portion 410. The center portion or pupil area 410 may be colored black to represent the pupil or tinted giving an appearance that the pupil is black.

In some embodiments, the center portion 410 may be clear or transparent or may be an empty space. This allows light to pass through the center portion 410 and stimulate the underlying nerves. Even though the patient may not be able to see, nerves that can detect light can be stimulated, thereby reducing atrophy of those nerves. In the event medical procedures are developed to restore eyesight to the patient now or in the future, those nerves in the eyes would still be intact and would not have lost any abilities or functioning as a result of the prosthetic iris.

The cornea 404 is dome-shaped with a base 420 and a first apex 422. A backing 409 may be attached to or formed with the base 420 of the cornea 404. The cornea 404 is preferably made of acrylic, such as PMMA.

The base 420 of the cornea 404 is defined by a circular rim 424 defining a plane. In the preferred embodiment, the diameter of the base 420 is approximately 12.5 mm. In some embodiments, the backing 409 may also be dome-shaped, defined by a concave outer surface 431 and a convex inner surface 432 defining a second apex 426 and curving towards and coaxially aligned with the first apex 422. Once assembled, the distance from the second apex 426 to the plane (as measured by a line perpendicular to the plane) may range from approximately 0 to 3 mm. The distance from the first apex 422 to the plane may be approximately 3 to 4 mm.

In a preferred embodiment, the second apex 426 is optimally curved to trade off natural-appearing depth of the iris beneath the first apex 422. Through much experimentation, it has been determined that a 1 mm distance from the second apex 426 to the plane in combination with a 4 mm distance from the first apex 422 to the plane is ideal in the majority of eye sockets requiring fitment of prosthetics.

The stem 430 is attached to or internally formed with the first apex 422 of the cornea 404. The stem 430 may be a cylindrical rod. In the preferred embodiment, the stem 430 has a diameter of approximately 2.5 mm and the length of approximately 9 mm. Based upon much experimentation, a preferred embodiment for the stem 430 taper is 0.05 mm to 0.07 mm, gradually and evenly away from the base 420. The tapering allows the final iris 400 to be released from its mold more satisfactorily than without the tapering.

In the preferred embodiment, sample iris 102 and the final iris 400 may be manufactured by a pressure casting process, an injection molding process, or an ultraviolet light cure process. In any case, after printing the iris image (i.e., the digitized iris print) 106 or 402, it is cut out and forced into a desired curve or shape (so that the printed surface is convex), such as with an embossing device that is designed to contour the iris, or an array of irises, under pressure while minimizing any handling of the iris 106 or 402. The iris or irises 106 or 402 may subsequently become fully plasticized with excess air bubbles removed or reduced. For example, the iris print 106 or 402 may be treated with an air void-displacing mixture of low viscosity (1 to 3 centipoise) liquid PMMA suitable for saturating the iris print 106 or 402, preferably within 10 seconds. In some embodiments, the iris print 106 or 402 may be placed floating in a PMMA coating material concave side up until the coating material diffuses from the print side to the concave side in order to enhance ultimate physical stability and durability of the fully plasticized iris image.

Once the iris print 106 or 402 is fully plasticized, the iris print is removed from the mixture and may be dried to touch by, for example, wiping or brushing. The iris print 106 or 402 can be fully dried under warm air stream or in an oven while preparing the custom iris mold for the casting, injection molding, or ultraviolet curing process. However, this step is optional.

For the pressure casting process, a concave mold (anterior mold) for the front or anterior side of the iris with the stem is created, and a convex mold (posterior mold) for the back side of the iris is created. The convex mold may be flat, semi-flat, or custom tailored to accommodate specific shapes of the patient's eye socket. An ultra-thin layer of silicone dental mold release can be applied to the concave mold to allow easier release of the iris.

A layer of foil may be used to cover the convex mold. The foil is trial-pressed tightly over the mold so that crinkling is eliminated. A circular alignment tool is used by aligning indexes in the convex mold. The iris print 106 or 402 is centered on the convex mold and a thick consistency (non-pourable yet tacky) specialty PMMA adhesive is used to completely and firmly attach the backside of the iris 102 or 400 to the iris print 106 or 402. This can be cured at moderate temperatures, for example, approximately 60 degrees C. to approximately 70 degrees C.

A slow batch of medium consistency PMMA dough is created and applied to the concave mold to fill the concavity and a hole for the stem. The convex mold is then pressed into the concave mold. A flat backing plate may be placed against the stem hole side of the concave mold to seal the stem sprue. The flat backing plate may have a suitable plastic membrane as necessary. The mated concave and convex molds are enclosed in a dental hydraulic press such that approximately 5% to approximately 10% of the hydraulic press remains open. A preferred embodiment is to use 0.5 mm spacers temporarily placed between mold halves to insure that sufficient PMMA dough remains for final mold closure. The PMMA dough is allowed to set for 10 to 15 minutes, and optimally 14 to 15 minutes, to achieve a "snappy" state of polymerization, which is known in the industry. Once the "snappy" state of polymerization is achieved, the hydraulic press is fully closed. In the preferred embodiment, the PMMA dough is fully polymerized in about 20 minutes at 70 degrees C. and then at 100 degrees C. for 20 minutes, for example, in a Liqisteam-e automatic machine.

In some embodiments, a posterior convex mold is not required. Rather, a flat mold back may be used to encapsulate a flat iris print 106 or 402 into the iris 102 or 400. For example, the iris print may be appropriately positioned on top of one or more foil layers. In the preferred embodiment, two layers of foil are used. PMMA dough is pressed into the anterior or concave mold. Then, the pre-positioned iris print 106 or 402 is pressed against the PMMA dough and the concave mold with the foil behind the iris print, and the molds are held together with a clamp. The mold is then cured in a wet pressure Liqisteam-e curing unit for 20 minutes at 70 degrees C. and 20 more minutes at 100 degrees C.

The sample iris 102 or the final iris 400 are cooled slowly. A slow reduction of temperature of the irises 102 or 400 helps prevent crazing that may otherwise occur. Crazing is a network of very fine residual stress-induced cracks that may occur on the surface of any plastic. As a result, cooling rates in the range of 1 to 5 degrees F. per minute are preferred, and more specifically, in the range of 2 to 3 degrees F. per minute appear optimal. The mold halves may be split apart when the temperature reaches about that of cold tap water.

Once fully cooled, the final, complete irises 404 are punched out. In some embodiments, the stem 111 or 430 may be tapered to facilitate its release from the mold. The diameter of the fully plasticized iris can be turned down or trimmed or the front of the iris can be thinned out as necessary for molding into a scleral shell.

In the injection molding process, after the iris print 106 or 402 has been fully plasticized and dried as discussed above, the injection feed system of either a horizontal or vertical injection molding machine can be charged with medical grade PMMA pellets. A silicon-based release formula can be applied to the injection molding cavities. The iris print 106, 402 is placed into a "cold" cavity side of the injection molding machine which is equipped with a suitably contoured convex mold for the backside of the iris. Simultaneously, the "hot" side of the injection mold is closed against the "cold" side mold and molten PMMA is injected into the work cavity under pressure against the front side of the digitized iris print. The mold can then be opened and the finished iris ejected from the hot side with compressed air. The fully plasticized iris is then prepared for molding into the scleral shell by turning down or trimming the diameter of the iris or thinning of the front of the iris.

Using the acrylic shell and the iris 400, the placement of the iris (the "gaze") on the mold is set. White acrylic is added to the mold to create the scleral shell around the iris 400 to create the prosthetic eye comprising the iris 400 surrounded by the white scleral shell. The prosthetic eye is cured and removed from the mold. The white plastic is then removed from over the iris to expose the limbus and create a blend from the iris to the sclera. The iris diameter is also matched within a tenth of a millimeter using iris diameter measurements taken digitally from patient photographs. The stem 430 is removed and the prosthetic eye is smoothed out. The vein pattern of the functioning eye is recreated in the prosthetic eye as a mirror image of the veins in the functioning eye, using, for example, tiny silk threads. In some embodiments, the scleral shell is hand-painted, incorporating any visual details of the functioning eye.

The patient can then follow up with the ocularist the following day or in 3 months, or some other time as is convenient for the patient. The ocularist can check the opening, alignment for visual eye contact, closure of the eye, anatomical function and secretions, and make sure that the surrounding tissues are not being irritated. The patient can continue to follow up with the ocularist as necessary (for example, every six months) to remove the prosthetic eye, clean it, polish it to a shine, and discuss a maintenance regimen.

The color of the iris is also made more accurate in the photograph by using a color checker card that white balances the photograph for the most accurate color. The color checker card also may be used to measure various eye structures like the pupil, iris, collarette, stroma, and limbus.

Therefore, a method of producing a color-matched iris for a prosthetic eye includes providing an array 100 of sample irises 102, for example, to an ocularist, having the ocularist compare the sample irises to the natural iris of the patient, having the ocularist select at least one sample iris having characteristics that match the natural eye, having the ocularist note and/or record the unique indicia associated with the selected sample iris, receiving at least one unique indicia of at least one sample iris having at least one unique characteristic match a corresponding characteristic of a natural eye of a patient, retrieving a digital image associated with at least one unique indicia, and printing the digital image to create a final iris. The array of sample irises may cover an entire spectrum of eye colors.

In some embodiments, a composite iris may be created by receiving multiple unique indicia to create the final iris. Each unique indicia may correspond with one or more unique characteristic matching the corresponding characteristic in the natural eye. Therefore, the body 112 of one iris may be combined with the limbus 113 of another iris, and an inner ring 115 of yet another iris to create a composite iris.

On a larger scale, a plurality of sample irises 102 can be distributed to a plurality of ocularists. The ocularists conduct their own comparisons with their own patients and send back the unique indicia associated with a particular characteristic to request the creation of the final iris as discussed above. As each request is received, the final irises corresponding to the requested unique indicia are retrieved from a database, printed, and the digitized iris print 402 sent back to the ocularist. In some embodiments, the digitized iris print 402 may be encapsulated into a final cornea before sending back to the ocularist. In some embodiments, the ocularists may encapsulate the digitized iris print 402 themselves.

The sample irises 102 may comprise a sample cornea 104, a sample digitized iris print 106 encapsulated in the cornea 104, and a unique indicia associated with the sample digitized iris print 106, wherein each sample iris has unique characteristics identifiable by the unique indicia.

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention not be limited by this detailed description, but by the claims and the equivalents to the claims appended hereto.

What is claimed is:

1. A method for producing a color-matched iris for a prosthetic eye, comprising:
    a. providing an array of sample irises, each sample iris comprising:
        i. a sample cornea;
        ii. a digitized iris print encapsulated in the sample cornea; and
        iii. a plurality of unique indicia associated with the digitized iris print, wherein each sample iris has a plurality of unique characteristics selected from the group consisting of: an iris body color, an inner ring color, a degree of how pronounced the inner ring is, an inner ring dimension, an outer ring color, a degree of how pronounced the outer ring is, and an outer ring dimension, said plurality of characteristics being identifiable by the plurality of unique indicia;
    b. receiving two or more unique indicia selected by matching at least one sample iris from the array of sample irises with a natural eye of a patient;
    c. retrieving a digital image associated with the two or more unique indicia; and
    d. printing the digital image to create a final iris.

2. The method of claim 1, wherein the array of sample irises covers an entire spectrum of eye colors.

3. The method of claim 1, further comprising receiving three or more unique indicia to create the final iris from a composite of unique characteristics, wherein each unique indicium corresponds with at least one unique characteristic matching a corresponding characteristic in the natural eye.

4. The method of claim 1, further comprising:
    a. distributing a plurality of arrays of sample irises to a plurality of ocularists;

b. receiving a plurality of unique indicia to print a plurality of final irises; and c. printing a plurality of final irises corresponding to the plurality of unique indicia.

5. The method of claim 1, wherein the digitized iris print comprises a transparent pupil area.

6. The method of claim 5, wherein the transparent pupil area is tinted giving an appearance that the pupil is black.

7. The method of claim 1, wherein the sample cornea comprises a tapered stem.

* * * * *